(12) United States Patent
Mori et al.

(10) Patent No.: US 7,569,373 B2
(45) Date of Patent: Aug. 4, 2009

(54) METHOD FOR COUNTING MEGAKARYOCYTES

(75) Inventors: Yusuke Mori, Kobe (JP); Toshihiro Mizukami, Kobe (JP); Tomohiro Tsuji, Kobe (JP); Yoshiro Ikeuchi, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 125 days.

(21) Appl. No.: 11/392,651

(22) Filed: Mar. 30, 2006

(65) Prior Publication Data

US 2006/0223138 A1    Oct. 5, 2006

(30) Foreign Application Priority Data

Mar. 30, 2005   (JP)   ............................. 2005-100140

(51) Int. Cl.
    *C12N 13/00*   (2006.01)
(52) U.S. Cl. ................... 435/173.9; 435/29; 435/288.7; 422/82.07
(58) Field of Classification Search ................ 435/40.5, 435/7.24; 436/175; 422/82.07
    See application file for complete search history.

(56) References Cited

U.S. PATENT DOCUMENTS

2004/0009471 A1*  1/2004  Cao  ............................. 435/5
2005/0003471 A1*  1/2005  Wang et al.  ................. 435/40.5
2005/0202400 A1*  9/2005  Tsuji et al.  ..................... 435/4

FOREIGN PATENT DOCUMENTS

EP    1 542 008 A1    6/2005

OTHER PUBLICATIONS

Aaron Tomer, et al "Flow Cytometric Analysis of Normal Human Megakaryocytes", Blood, vol. 71, No. 5, May 1988, pp. 1244-1252.
Diamond et al, "*Flow Cytometry in the Diagnosis and Classification of Malignant Lymphoma and Leukemia*", Cancer, American Cancer Society, vol. 50, No. 6, Sep. 15, 1982, pp. 1122-1135, XP008064994.
Petriz et al, "*Relevance of Forward Scatter and Side Scatter in Aneuploidy Detection By Flow Cytometry*", Analytical Cellular Pathology, Elsevier Science, Amsterdam, NL, vol. 10, No. 3, May 1996, pp. 243-252, XP008064996.

* cited by examiner

*Primary Examiner*—Ralph Gitomer
(74) *Attorney, Agent, or Firm*—Sughrue Mion, PLLC (57) ABSTRACT

A method for counting megakaryocytes in a specimen is described. In the method, first, erythrocytes in the specimen are lysed and nucleic acid in the megakaryocytes is stained with a fluorescent dye, and thereby, a measurement sample is prepared. Next, the cells in the measurement sample are irradiated with excited light so that the forward scattered light, the side scattered light and the fluorescence, which are emitted from the cells, are detected. Megakaryocytes are identified on the basis of the detected forward scattered light, the fluorescence and the side scattered light. Then, the identified megakaryocytes are counted.

12 Claims, 4 Drawing Sheets

METHOD FOR COUNTING MEGAKARYOCYTES

BACKGROUND OF THE INVENTION

1. Field of the Invention

The present invention relates to a method and an apparatus for counting megakaryocytes.

2. Description of the Related Art

In the field of clinical examination, significantly useful information for diagnosing diseases can be obtained by identifying and counting megakaryocytes. Usually, a constant number of megakaryocytes exist in the normal bone marrow. Megakaryocytes are mother cells of thrombocytes, and the number of megakaryocytes may fluctuate due to disease in some cases, for example, when there is a reduction or an increase in the number of thrombocytes in the peripheral blood. Accordingly, identifying and counting these megakaryocytes is useful for obtaining information for the presence of a disease. The number of megakaryocytes increases, for example, in idiopathic thrombocytopenic purpura (ITP), thrombotic thrombocytopenic purpura (TTP), essential thrombocytopenia and chronic myelogenous leukemia, and the number of megakaryocytes decreases in aplastic anemia.

As for a conventional method for counting megakaryocytes, generally, bone marrow aspirate is appropriately dyed and the obtained sample is transferred to a hemocyte calculating board, such as a Fuchs-Rosenthal calculating board, so that the megakaryocytes can be observed under a microscope and identified and counted. Megakaryocytes are characterized by their form; by having large cells, polynucleic cells, and blurred-looking cytoplasm. However, the standard for recognizing megakaryocytes is very ambiguous, and additionally, the ratio of megakaryocytes in the bone marrow is very low. Therefore, determination of megakaryocytes through visual examination is highly inconsistent and differs depending on the measuring person.

In recent years, identifying and counting of megakaryocytes using the thesis of flow cytometer has been attempted. According to the document by Tomer et al (Tomer et al, Blood, 1988; 71: 1244-1252), for example, megakaryocytes are identified and counted by a two-color measuring method using fluorescence-labeled anti-platelet antibodies and propidium iodide. Concretely, first, mononuclear cells are separated from bone marrow aspirate. The obtained sample containing mononuclear cells contains megakaryocytes, and the megakaryocytes in this sample are labeled with fluorescence-labeled anti-platelet antibodies. Next, the cells in the sample are fixed with 2% of paraformaldehyde, and then, dyed with propidium iodide. Thus, the obtained sample is measured with a flow cytometer, so that the megakaryocytes can be identified and counted. According to this method, separation of molecular cells makes the operation complex, and measurement requires much time. In addition, there is a possibility that part of the megakaryocytes will not be collected during the separation operation, and thus, the megakaryocytes cannot be identified and counted precisely.

Meanwhile, US Patent Application Publication No. 2005-0003471 describes a method for measuring megakaryocytes using an automatic hemocyte counting apparatus. Concretely, first, Dami cells, which are a strain of megakaryocyte based cells, are cultivated so as to obtain a specimen containing megakaryocytes, or purified CD34 positive cells are cultivated so as to obtain a specimen containing megakaryocytes. Then, the obtained specimen is measured with an automatic hemocyte counting apparatus, and megakaryocytes appear in the obtained two-dimensional distributional diagram. In addition, the two-dimensional distribution diagram that is obtained by measuring a specimen containing purified megakaryocytes and the two-dimensional distribution diagram that is obtained by measuring a specimen that does not contain megakaryocytes are compared, and thereby, a region where megakaryocytes appear can be determined in the two-dimensional distribution diagram. However, various cells other than megakaryocytes are included in bone marrow aspirate that has been extracted from a living body. In particular, the regions where plasmacytes, which appear in bone marrow aspirate that has been extracted from a patient having multiple myeloma appear, are quite similar to those of megakaryocytes in the two-dimensional distribution diagram.

Therefore, a method by which megakaryocytes can be measured more precisely by separating megakaryocytes that are included in bone marrow aspirate from other cells, such as plasmacytes, has become required.

SUMMARY OF THE INVENTION

An object of the present invention is to provide a method and an apparatus for counting megakaryocytes more precisely.

A first aspect of the present invention relates to a method for counting megakaryocytes in a specimen, comprising the steps of: preparing a measurement sample by lysing erythrocytes in the specimen and staining nucleic acid in the megakaryocytes with a fluorescent dye; irradiating cells in the measurement sample with excited light; detecting forward scattered light, side scattered light and fluorescence which is emitted from the cells; identifying megakaryocytes on the basis of the detected forward scattered light, side scattered light and fluorescence; and counting the identified megakaryocytes.

A second aspect of the present invention relates to an apparatus for counting megakaryocytes, comprising: a easurement sample preparing part for preparing a measurement sample by mixing a specimen that includes megakaryocytes, a lysing reagent for lysing erythrocytes, and a nucleic acid fluorescent dye for staining megakaryocytes; a light source for irradiating cells in the measurement sample with excited light; a first scattered light detector for detecting forward scattered light which is emitted from cells; a second scattered light detector for detecting side scattered light which is emitted from cells; a fluorescence detector for detecting fluorescence which is emitted from cells; and an analyzing part for identifying megakaryocytes on the basis of the detected forward scattered light, fluorescence and side scattered light, and counting the identified megakaryocytes.

BRIEF DESCRIPTION OF THE DRAWINGS

FIG. 3-A is a first two-dimensional distribution diagram of which the two axes are the intensity of forward scattered light and the intensity of side scattered light which have been obtained in a measured example;

FIG. 3-B is a second two-dimensional distribution diagram of which the two axes are the intensity of side scattered light and the intensity of fluorescence which have been obtained in the measured example;

FIG. 4-A is a first two-dimensional distribution diagram of which the two axes are the intensity of forward scattered light and the intensity of side scattered light which have been obtained in the measured example;

FIG. 4-B is a second two-dimensional distribution diagram of which the two axes are the intensity of side scattered light and the intensity of fluorescence which have been obtained in the measured example;

FIG. 5-A is a first two-dimensional distribution diagram of which the two axes are the intensity of forward scattered light and the intensity of side scattered light which have been obtained in the measured example;

FIG. 5-B is a second two-dimensional distribution diagram of which the two axes are the intensity of side scattered light and the intensity of fluorescence which have been obtained in the measured example.

DESCRIPTION OF THE PREFERRED EMBODIMENTS

Megakaryocytes are cells which are very large in comparison with other blood cells. Therefore, megakaryocytes and other blood cells can be distinguished on the basis of forward scattered light, which reflects the sizes of cells. It is difficult, however, to distinguish blood cells (for example, plasmacytes), of which the size is similar to that of megakaryocytes, from megakaryocytes on the basis of forward scattered light. Therefore, the inventors focused attention on the following properties concerning the nuclei of megakaryocytes: the size of nuclei is large; the form of the nuclei has a significant irregularity in such a manner that nuclei which have significant recesses and are lobulated overlap each other; and the amount of nucleic acid that is included in nuclei is great. Thus, the inventors have discovered a method for precisely counting megakaryocytes by distinguishing megakaryocytes from blood cells, of which the size is similar to that of megakaryocytes, on the basis of side scattered light, which reflects the structure of the inside of cells, and fluorescence, which reflects the amount of nucleic acid in cells that are stained with a nucleic acid fluorescent dye.

Concretely, first, erythrocytes, in a specimen that includes megakaryocytes, are lysed and nucleic acid in the megakaryocytes is stained with a fluorescent dye, and thereby, a measurement sample is prepared. Next, the cells in the measurement sample are irradiated with excited light so that the forward scattered light, the side scattered light and the fluorescence, which are emitted from the cells, are detected. Megakaryocytes are identified on the basis of the detected forward scattered light, the fluorescence and the side scattered light. Then, the identified megakaryocytes are counted. Here, "megakaryocytes" and "cells of which the sizes are different from that of megakaryocytes" are distinguished from each other on the basis of the forward scattered light, and "megakaryocytes" and "cells of which the size is similar to that of megakaryocytes" are distinguished from each other on the basis of the side scattered light and the fluorescence. As a result of this, the megakaryocytes can be precisely counted by distinguishing them from other cells such as plasmacytes.

As for the specimen that includes megakaryocytes, bone marrow aspirate can be cited. Bone marrow aspirate is extracted from marrow, which produces blood cells, by means of bone marrow puncture. Bone marrow aspirate includes megakaryocytes and other blood cells. In the case where bone marrow aspirate is used as a specimen, it is preferable to filter it with a nylon mesh having an appropriate pore diameter in advance due to the existence of a large number of impurities such as bone particles and fibrin lumps. Through this operation, megakaryocytes pass through the nylon mesh while impurities cannot pass through it, and therefore, the impurities can be removed from the specimen.

In order to prepare a measurement sample from the specimen, a lysing reagent for lysing erythrocytes in the specimen and a nucleic acid fluorescent dye for staining nucleic acid in megakaryocytes with a fluorescent dye can be used.

The lysing reagent is used in order to lyse the erythrocytes in the specimen to an extent that it does not hinder the measurement, and in order to create pores, which are sufficient for at least the dye molecules to permeate, in the cell membranes of the megakaryocytes which are the objects of measurement. As for the lysing reagent that is used for this purpose, a solution, which includes at least one type of cationic surfactant, at least one type of nonionic surfactant and a buffering agent for keeping pH constant, can be cited as an example. The pH of the solution is in a range from pH 4.5 to 11.0, and preferably, from pH 5.0 to 10.0.

As for the cationic surfactant, a quaternary ammonium salt type surfactant or a pyridinium salt type surfactant is preferable. As for the quaternary ammonium salt type surfactant, a surfactant having the total carbon number of 9 to 30, which is represented by the following Chemical Formula 1, can be cited.

Chemical Formula 1

As for the pyridinium salt type surfactant, a surfactant having the total carbon number of 11 to 30, which is represented by the following Chemical Formula 2, can be cited.

Chemical Formula 2

Here, in Chemical Formulas 1 and 2, R1 indicates an alkyl group having a carbon number of 6 to 18 or an alkenyl group having a carbon number of 6 to 18. In Chemical Formula 1, R2 and R3 are an alkyl group having a carbon number of 1 to 4 or an alkenyl group having a carbon number of 1 to 4. In Chemical Formula 1, R4 is an alkyl group having a carbon number of 1 to 4, an alkenyl group having a carbon number of 1 to 4 or a benzyl group. In Chemical Formulas 1 and 2, X is a halogen atom. As for the alkyl group or the alkenyl group of R1, hexyl, octyl, decyl, dodecyl, tetradecyl and the like can be cited, and in particular, an alkyl group with a straight chain such as octyl, decyl, or dodecyl is preferable. In addition, as for the alkyl group or the alkenyl of R2 and R3, methyl, ethyl, propyl, butyl and the like can be cited, and in particular, an alkyl group having a carbon number of 1 to 3 such as methyl, ethyl or propyl is preferable. Furthermore, the alkyl group or the alkenyl group of R4, methyl, ethyl, propyl, butyl and the like can be cited, and in particular, an alkyl group having a carbon number of 1 to 3 such as methyl, ethyl or propyl is preferable. The concentration of the cationic surfactant is generally 200 ppm to 1500 ppm, preferably 500 ppm to 1000 ppm, and more preferably, 600 ppm to 800 ppm.

As for the nonionic surfactant, a polyoxy ethylene based nonionic surfactant, in the following formula, is preferable: R1-R2-(CH$_2$CH$_2$O)n-H. Here, in the formula, R1 is an alkyl group having a carbon number of 8 to 25, an alkenyl group having a carbon number of 8 to 25 or an alkynyl group having a carbon number of 8 to 25. R2 is O, COO or Chemical Formula 3.

Chemical Formula 3 n indicates an integer from 10 to 50.

The concentration of the nonionic surfactant is generally 500 ppm to 3000 ppm, preferably 1000 ppm to 2500 ppm, and more preferably, 1500 ppm to 2000 ppm.

Furthermore, at least one organic acid or a salt thereof may be contained in the lysing reagent. The above described organic acid or the salt thereof has at least one aromatic ring within the molecule. As for this organic acid or the salt thereof, benzoic acid, phthalic acid, hippuric acid, salicylic acid, p-amino benzenesulfonic acid, benzenesulfonic acid and salts of these can be appropriately used. The concentration of the organic acid or the salt thereof is generally 10 mM to 100 mM, preferably 15 mM to 50 mM, and more preferably, 20 mM to 30 mM.

The pH of the lysing reagent is from 4.5 to 11.0, preferably from 5.0 to 10.0. The lysing reagent includes, for example, a buffering agent such as citrate, HEPES or phosphate in order to keep the pH constant. The concentration of the buffering agent is generally 5 mM to 100 mM, and preferably 10 mM to 50 mM. Here, in the case where the above-described organic acid works as a buffering agent, a buffering agent is not an essential component.

A lysing reagent, as described above, is added to a specimen so as to lyse the erythrocytes in the specimen, and to process the megakaryocytes so that a dye can permeate the cell membranes of the megakaryocytes. Therefore the megakaryocytes can be stained with a nucleic acid fluorescent dye. In the case where bone marrow aspirate is used as a specimen, for example, the mixture ratio of the bone marrow aspirate to the lysing reagent is generally 1:20 to 1:200, preferably 1:30 to 1:100, and more preferably, 1:40 to 1:60.

The nucleic acid fluorescent dye is a fluorescent dye which stains specifically nucleic acid within cells. As for the nucleic acid fluorescent dye, a dye having the structure of the following Chemical Formula 4 can be used, though different dyes may be used depending on the wavelength of the light source.

Chemical Formula 4

In Chemical Formula 4, R1 is a hydrogen atom or an alkyl group. R2 and R3 are a hydrogen atom, a lower alkyl group or a lower alkoxy group. R4 is a hydrogen atom, an acyl group or an alkyl group. Z is sulfur, oxygen or carbon having a lower alkyl group. n is 0, 1 or 2. X— is an anion.

From among the above described nucleic acid fluorescent dyes, dyes, where at least either R1 or R4 is an alkyl group having a carbon number of 6 to 18, are preferable. Pigments where the carbon number of the alkyl group of R1 or R4 is 6, 8 or 10 are particularly preferable. In addition, the lower alkyl group or the lower alkoxy group of R2 and R3 means an alkyl group with a straight chain having a carbon number of 1 to 8 or an alkoxy group with a straight chain having a carbon number of 1 to 8, and is preferably a methyl group, a methoxy group, an ethyl group or an ethoxy group. Anions, which are appropriate for X—, include halogen ions such as F—, Cl—, Br— and I—, CF$_3$SO$_3$—, BF$_4$— and the like. As for Z, a sulfur atom, an oxygen atom or a carbon atom that is substituted by a lower alkyl group such as a methyl group, an ethyl group or an isopropyl group is preferable. In addition, in the case where a red semiconductor laser diode is used as a light source for the measurement, a nucleic fluorescent dye where R1 is a methyl group, R2 and R3 are a hydrogen atom, R4 is an n-octyl group, n is 1, Z is a sulfur atom and X is CF$_3$SO$_3$— is particularly appropriate. (Hereafter, this nucleic acid fluorescent dye is referred to as a dye compound A.)

As for other types of nucleic acid fluorescent dyes, propidium iodide, N-methyl-4-(1-pylene) vinyl-propidium iodide, ethidium bromide, TOTO-1, TOTO-3, YOYO-1, YOYO-3, BOBO-1, BOBO-3, ethidium homodimer-1 (EthD-1), ethidium homodimer-2 (EthD-2), POPO-1, POPO-3, BO-PRO-1, YO-PRO-1, TO-PRO-1 and the like can be cited as examples.

The nucleic acid fluorescent dye can be appropriately selected depending on the wavelength of the light source that is used for the measurement. Though the concentration of the dye differs depending on the type of dye that is used, it is generally 0.0001 ppm to 1000 ppm, preferably 0.01 ppm to 100 ppm, and more preferably, 0.1 ppm to 10 ppm. Here, these concentrations are the concentrations when the lysing reagent and the nucleic acid fluorescent dye are mixed.

In the case where a lysing reagent and a nucleic acid fluorescent dye, as those described above, are used in the preparation for a measurement sample, a reagent comprising a lysing reagent containing a nucleic acid fluorescent dye and a specimen may be mixed so that a measurement comprising is prepared. In addition, the first reagent comprising a lysing reagent, the second reagent comprising a nucleic acid fluorescent dye and a specimen may be mixed so that a measurement sample is prepared. The order of mixing the first reagent, the second reagent and the specimen is not particularly limited to this. For example, the first reagent and the second reagent may be mixed, and then, this mixture and the specimen may be mixed. Alternatively, the first reagent and the specimen may be mixed, and then, this mixture and the second reagent may be mixed.

A measurement sample that is prepared as described above is irradiated with excited light. Thus, forward scattered light, side scattered light and fluorescence are detected from the cells in the measurement sample. In the case where a flow cytometer is used for measuring, for example, the prepared measurement sample is led to a flow cell of the flow cytometer. Then, the measurement sample, which is flowing through the flow cell, is irradiated with excited light, and forward scattered light, side scattered light and fluorescence, which are emitted from the cells in the measurement sample, are detected.

Figure 1:
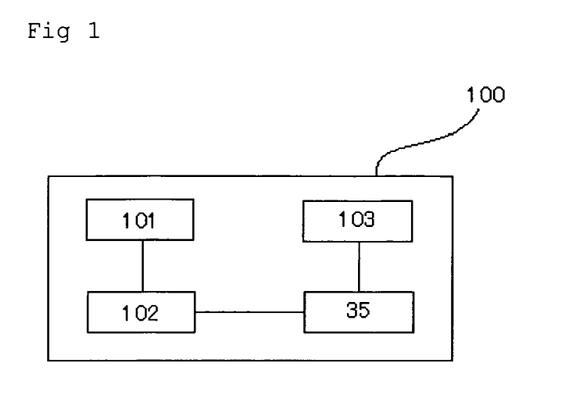
FIG. 1 is a diagram showing the configuration of a megakaryocyte counting apparatus according to an embodiment of the present invention.

FIG. 1 is a diagram showing an example of the configuration of a megakaryocyte counting apparatus according to the present embodiment. A megakaryocyte counting apparatus 100 has a measurement sample preparing part 101 where a measurement sample can be prepared from a specimen, a detection part 102 for measuring the measurement sample that has been prepared in measurement sample preparing part 101, an analyzing part 35 for analyzing a signal that has been detected by detection part 102 and a display part 103 for displaying the results of analysis by analyzing part 35.

Figure 2:
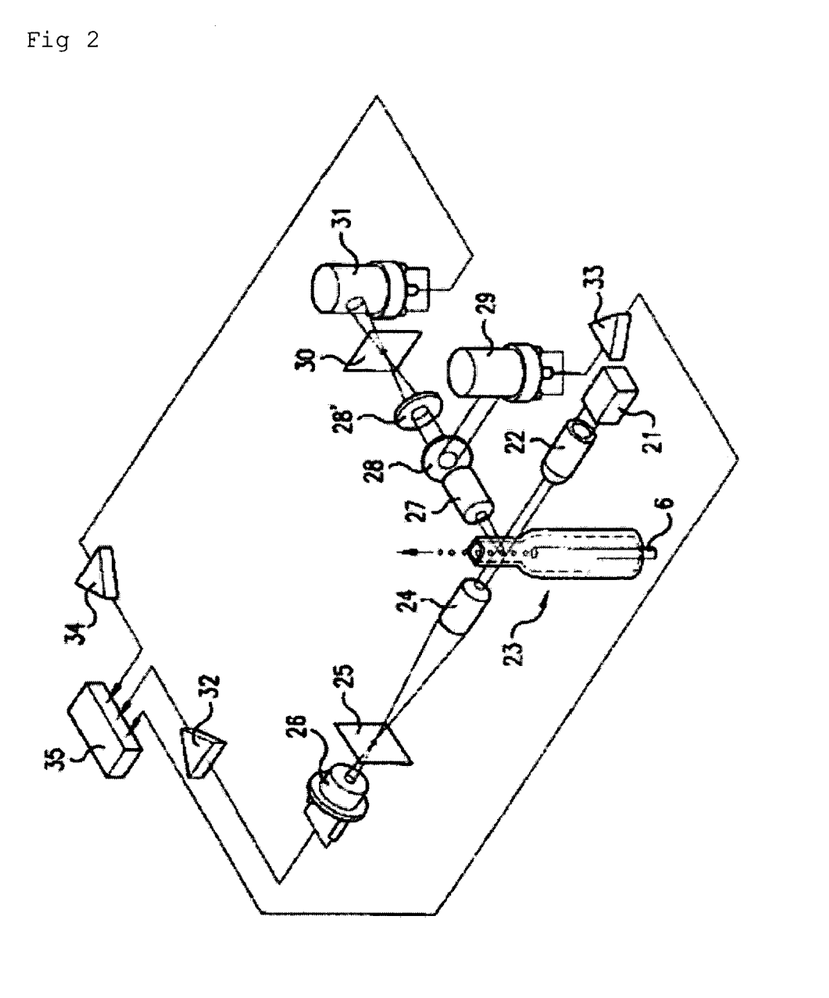
FIG. 2 is a diagram showing an example of an optical system of a flow cytometer that is used as a detection part in the megakaryocyte counting apparatus according to an embodiment of the present invention.

FIG. 2 shows an example of an optical system of a flow cytometer that is used as detection part 102. In FIG. 2, an orifice portion in a sheath flow cell 23 is irradiated with excited light that has been emitted from a light source (for example, laser diode) 21 via a collimating lens 22. The light source is not particularly limited, and an argon laser, a He—Ne laser, a semiconductor laser or the like is used.

Forward scattered light that is emitted from the cells, which are discharged from a nozzle 6 and pass through the orifice portion, enters into a forward scattered light detector (photodiode) 26 via a condenser lens 24 and a pinhole plate 25.

Meanwhile, side scattered light that is emitted from the cells which pass through the orifice portion enters into a side scattered light detector (photo multiplier tube) 29 via a condenser lens 27 and a dichroic mirror 28. Side fluorescence that is emitted from the cells, which pass through the orifice portion, enters into a side fluorescence detector (photo multiplier tube) 31 via condenser lens 27, dichroic mirror 28, a filter 29 and a pinhole plate 30. Here, megakaryocytes are cells having a larger amount of nucleic acid in comparison with other blood cells, and therefore, the intensity of fluorescence that is detected from the megakaryocytes that have been stained with a nucleic acid fluorescent dye is high. Therefore, it is preferable to adjust the system so that the sensitivity of the fluorescence detector is lower than in a usual case where leukocytes are measured, and megakaryocytes can be measured.

A signal of forward scattered light that is outputted from forward scattered light detector 26 is amplified by an amplifier 32 so as to be inputted into analyzing part 35. A signal of side scattered light that is outputted from side scattered light detector 29 is amplified by an amplifier 33 so as to be inputted into analyzing part 35. A signal of side fluorescence that is outputted from side fluorescence detector 31 is amplified by an amplifier 34 so as to be inputted into analyzing part 35.

Analyzing part 35 makes a first two-dimensional distribution diagram of which the two axes are the intensity of forward scattered light and the intensity of side scattered light, and specifies a first megakaryocyte region in the first two-dimensional distribution diagram. Furthermore, analyzing part 35 makes a second two-dimensional distribution diagram of which the two axes are the intensity of side scattered light and the intensity of fluorescence, and specifies a second megakaryocyte region in the second two-dimensional distribution diagram. Then, the cells, which appear within the first megakaryocyte region and appear within the second megakaryocyte region, are counted as megakaryocytes, followed by a desired arithmetic operation, and thus, the results of the counting and the operation are displayed on display part 103.

Megakaryocytes are cells which are very large in comparison with other blood cells, and therefore, the intensity of the forward scattered light is increased. Furthermore, the nuclei of megakaryocytes have a large size, and the form of the nuclei has a significant irregularity in such a manner that nuclei which have significant recesses and are lobulated overlap each other, and therefore, the intensity of side scattered light is increased. In addition, megakaryocytes have a very large amount of nucleic acid, and therefore, the intensity of fluorescence of the megakaryocytes that have been stained with a nucleic acid fluorescent dye is increased.

Figure 3:
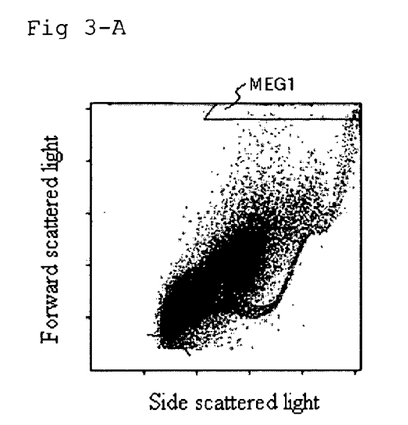

Accordingly, a first two-dimensional distribution diagram of which the two axes are the intensity of forward scattered light and the intensity of side scattered light is made, the region where the intensity of forward scattered light and the intensity of side scattered light are high is specified as a first megakaryocyte region (for example, region MEG1 in FIG. 3-A) in the first two-dimensional distribution diagram, and the cells that appear within the first megakaryocyte region are counted, and thereby, the megakaryocytes can be counted. In the case where a specimen includes cells such as plasmacytes of which the size is similar to that of megakaryocytes, however, some plasmacytes may be mixed into the above described region, and the number of the megakaryocytes is erroneously indicated at a higher value. Therefore, a second two-dimensional distribution diagram of which the two axes are the intensity of side scattered light and the intensity of fluorescence is made, and a region where the intensity of side scattered light is high and the intensity of fluorescence is high is specified as a second megakaryocyte region (for example, region MEG2 in FIG. 3-B) in the second two-dimensional distribution diagram. Then, the cells, which appear within the first megakaryocyte region and appear within the second megakaryocyte region, are counted as megakaryocytes. As a result of this, the megakaryocytes can be precisely counted.

Here, the number of megakaryocytes may be obtained in accordance with a method as described below. First, a first two-dimensional distribution diagram of which the two axes are the intensity of forward scattered light and the intensity of side scattered light is made, and a region where the intensity of forward scattered light and the intensity of side scattered light are high is specified as a first megakaryocyte region in the first two-dimensional distribution diagram. Then, a second two-dimensional distribution diagram of which the two axes are the intensity of side scattered light and the intensity of fluorescence is additionally made for the cells which appear in the first megakaryocyte region, a region where the intensity of side scattered light is high and the intensity of fluorescence is high is specified as a second megakaryocyte region in the second two-dimensional distribution diagram, and the cells within the second megakaryocyte region are counted as megakaryocytes.

Furthermore, the number of megakaryocytes may be found in accordance with a method as described below. First, a first two-dimensional distribution diagram of which the two axes are the intensity of side scattered light and the intensity of fluorescence is made, and a region where the intensity of side scattered light is high and the intensity of fluorescence is high is specified as a first megakaryocyte region in the first two-dimensional distribution diagram. Then, a second two-dimensional distribution diagram of which the two axes are the intensity of forward scattered light and the intensity of side scattered light is additionally made for the cells which have appeared in the first megakaryocyte region, a region where the intensity of forward scattered light and the intensity of side scattered light is high is specified as a second megakaryocyte region in the second two-dimensional distribution diagram, and the cells within the second megakaryocyte region are counted as megakaryocytes.

Here, though in the above described method, a two-dimensional distribution diagram of which the two axes are the intensity of forward scattered light and the intensity of side scattered light is made, the method is not limited to this. A particle size distribution diagram of which the horizontal axis is the intensity of forward scattered light, and of which the longitudinal axis is the number of cells can be used instead of the two-dimensional distribution diagram In this case, a predetermined threshold is set for the intensity of forward scattered light, and cells which indicate the intensity of forward scattered light of not less than this threshold can be identified as megakaryocytes.

In summary, in the present embodiment, megakaryocytes are identified on the basis the detected forward scattered light, fluorescence and side scattered light. More concretely, (1) a first cell group that includes megakaryocytes is specified on the basis of forward scattered light which reflects the sizes of cells,
(2) a second cell group that includes megakaryocytes is specified on the basis of side scattered light which reflects the information on the inside of the cells, and on the basis of fluorescence, which reflects the amount of nucleic acid, and
(3) the cells which belong to the first cell group and to the second cell group are identified as megakaryocytes.

In addition, a region having predetermined intensity of scattered light and intensity of fluorescence is specified as a region of cells having a nucleus (for example, region NC in FIG. 3-B, region NC includes region MEG2 in FIG. 3-B) in the two-dimensional distribution diagram of which the two axes are the intensity of side scattered light and the intensity of fluorescence, cells within this region are counted as cells having a nucleus, and the ratio of megakaryocytes in the cells having a nucleus can be found from the number of cells having a nucleus and the number of megakaryocytes.

In the following, a measurement example where megakaryocytes are measured is shown.

EXAMPLE (Preparation of Specimen)

Bone marrow aspirate was filtered through a nylon mesh (pore diameter 100 μm) so that impurities such as bone particles were removed, and thereby, a specimen containing megakaryocytes was prepared. Measurement of megakaryocytes was carried out on 33 specimens.

(Preparation of Reagent)

| Lysing reagent | |
|---|---|
| HEPES (commercially available product) | 10 mM |
| Potassium hydrogen phthalate (commercially available product) | 20 mM |
| BC30TX (POE (30) cetyl ether) (Nikko Chemicals Co., Ltd.) | 1850 ppm |
| Lauryl trimethyl ammonium chloride (commercially available product) | 650 ppm |
| Purified water | 1 L |
| pH was adjusted to 7.0 with NaOH | |
| Dye Liquid Containing Nucleic Acid Fluorescent Dye | |
| Pigment compound A | 27.5 ppm |
| Ethylene glycol | 1 L |

(Measurement)

980 μL of lysing reagent, 20 μL of dye liquid and 20 μL of a specimen containing megakaryocytes were mixed, and this mixture was made to react for 30 seconds at 40° C., and thus, a measurement sample was prepared. After that, the measurement sample was measured using a flow cytometer having a red semiconductor laser diode as a light source, so that, side scattered light, forward scattered light and fluorescence could be detected.

Next, a first two-dimensional distributional diagram of which the two axes are the intensity of forward scattered light and the intensity of side scattered light was made, and a region where the intensity of forward scattered light and the intensity of side scattered light are high in the first two-dimensional distribution diagram was designated as a first megakaryocyte region (region MEG1). Furthermore, a second two-dimensional distribution diagram of which the two axes are the intensity of side scattered light and the intensity of fluorescence was made, and a region where the intensity of side scattered light is high and the intensity of fluorescence is high in the second two-dimensional distribution diagram was designated as a second megakaryocyte region (region MEG2). Cells, which appear within regions MEG1 and MEG2, were counted as megakaryocytes. Meanwhile, in a contrasting method, a specimen containing megakaryocytes was stained with a Turk's solution, transferred to a Fuchs-Rosenthal hemocyte calculating board, and the megakaryocytes were counted through visual examination.

Figure 4:
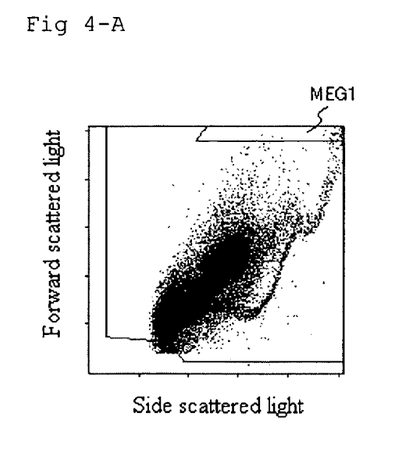
Figure 5:
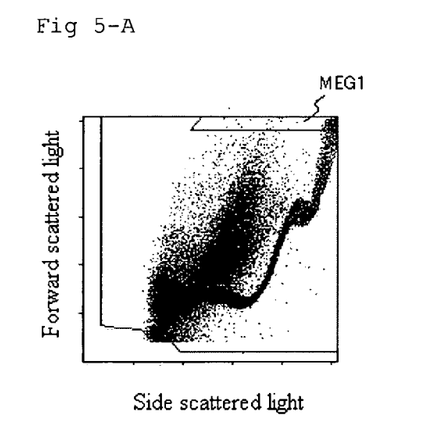

FIGS. 3, 4 and 5 are two-dimensional distribution diagrams of three specimens from among the thirty-three specimens which were used for the measurement. In particular, FIG. 5 shows the two-dimensional distribution diagram of a specimen containing plasmacytes. FIGS. 3-A, 4-A and 5-A are the first two-dimensional distribution diagrams, and MEG1 in the diagrams shows a first megakaryocyte region. FIGS. 3-B, 4-B and 5-B are the second two-dimensional distribution diagrams, and MEG2 in the diagrams shows a second megakaryocyte region, and NC shows a region of cells having a nucleus.

It was found, by comparing FIGS. 3-B, 4-B and 5-B, that the region where plasmacytes appear and the region where megakaryocytes appear (MEG2) were different.

Figure 6:
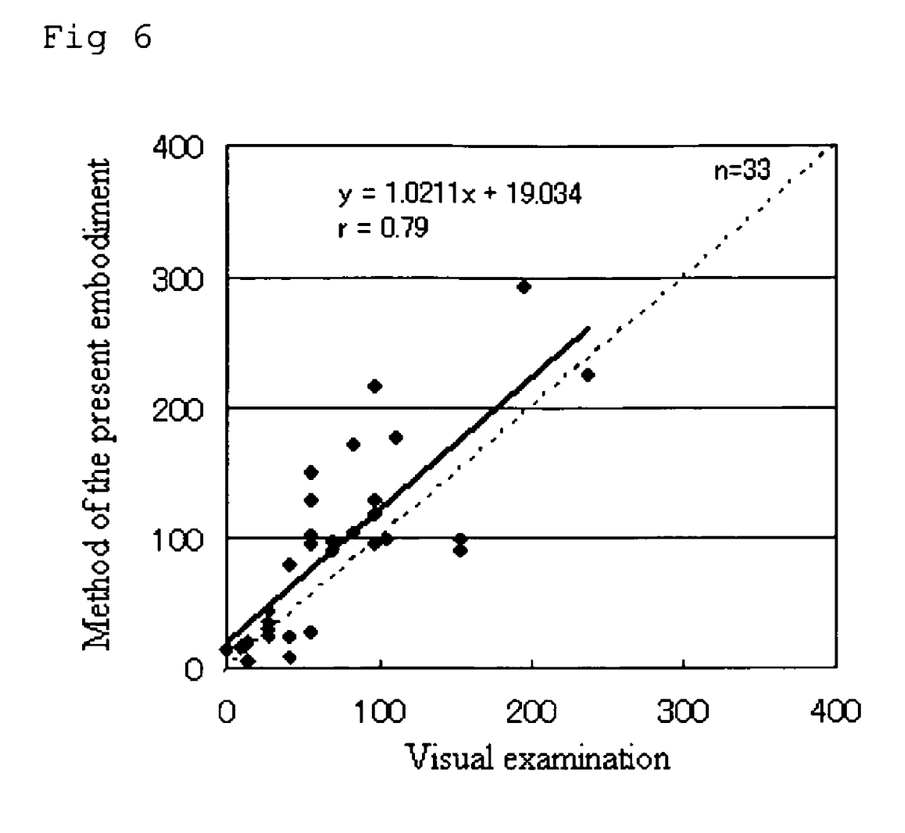
FIG. 6 is a graph showing the relationship between the number of megakaryocytes that have been obtained in the measured example and the number of megakaryocytes that have been obtained through visual examination.

Furthermore, the correlation between the number for megakaryocytes that was obtained in accordance with the method of the present embodiment and the number for megakaryocytes that was obtained through visual examination was checked for the thirty-three specimens used for the measurement (FIG. 6). The regression line formula became $y=1.0211x+19.034$, and the correlation coefficient became $r=0.79$, and thus, the correlation was excellent.

According to the method and apparatus for counting megakaryocytes of the present embodiment, megakaryocytes can be counted easily, quickly and precisely using an automatic hemocyte analyzing apparatus adopting a flow cytometry method. Therefore it is useful for automating megakaryocyte examination, which, so far invariably relied on visual examination.

What is claimed is:

1. A method for counting megakaryocytes in a bone marrow sample which comprises:

preparing a measurement sample by lysing erythrocytes in the bone marrow sample and staining nucleic acid in the megakaryocytes with a fluorescent dye;

irradiating the measurement sample with light from an optical system;

detecting forward scattered light, side scattered light and fluorescence which is emitted from cells in the irradiated measurement sample; and counting megakaryocytes in the irradiated measurement sample comprising:

specifying first cells containing megakaryocytes from the cells in the irradiated measurement sample by detected forward scattered light, specifying second cells containing megakaryocytes from the cells in the same irradiated measurement sample as the first cells by detected side scattered light and by detected fluorescence; and counting megakaryocytes which belong commonly to both of the specified first cells and the specified second cells.

2. The method according to claim 1, wherein the measurement sample preparing step is performed by mixing the bone marrow, a lysing reagent for lysing erythrocytes, and the fluorescent dye.

3. The method according to claim 2, wherein the measurement sample preparing step is performed by first mixing the bone marrow and the lysing reagent, and then adding the fluorescent dye.

4. The method according to claim 1, further comprising a step of introducing the measurement sample into a flow cell of a flow cytometer, and wherein the irradiating step is performed by irradiating the measurement sample that flows through the flow cell with light.

5. The method according to claim 1, wherein the specifying first cells step further comprises preparing a particle size distribution diagram by plotting intensity of the detected forward scattered light against particle size to specify the first cells on the particle size distribution diagram;

the specifying second cells step further comprises preparing a two-dimensional distribution diagram by plotting the intensity of the detected side scattered light against intensity of the detected fluorescence to specify the second cells on the two-dimensional distribution diagram; and the counting step comprises counting cells, as megakaryocytes, which are specified in both the first and second cells.

6. The method according to claim 1, further comprising:
(a) identifying cells having a nucleus by detected fluorescence and by detected side scattered light; and
(b) counting the cells of (a) having a nucleus.

7. The method according to claim 6, further comprising the step of calculating a ratio of megakaryocytes from the number of megakaryocytes and the number of cells having a nucleus.

8. The method according to claim 1, wherein the specifying first cells step is further performed by specifying the first cells by detected side scattered light.

9. A method for counting megakaryocytes in bone marrow which comprises:
preparing a measurement sample by lysing erythrocytes in the bone marrow and staining nucleic acid in the megakaryocytes with a fluorescent dye;
irradiating the measurement sample with light from an optical system;
detecting forward scattered light, side scattered light and fluorescence which is emitted from cells in the irradiated measurement sample;
specifying first cells containing megakaryocytes from the cells in the irradiated measurement sample by detected forward scattered light;
specifying second cells from the first cells in the same irradiated measurement sample as the first cells by detected side scattered light and by detected fluorescence; and
counting megakaryocytes which belong commonly to both of the specified first cells and the specified second cells.

10. The method according to claim 9, wherein the specifying first cells step is further performed by specifying the first cells by detected side scattered light.

11. A method for counting megakaryocytes in bone marrow which comprises:
preparing a measurement sample by lysing erythrocytes in the bone marrow and staining nucleic acid in the megakaryocytes with a fluorescent dye;
irradiating the measurement sample with light from an optical system;
detecting forward scattered light, side scattered light and fluorescence which is emitted from cells in the irradiated measurement sample;
specifying first cells containing megakaryocytes from the cells in the irradiated measurement sample by detected side scattered light and by detected fluorescence;
specifying second cells from the first cells in the same irradiated measurement sample as the first cells by detected forward scattered light; and
counting megakaryocytes which belong commonly to both of the specified first cells and the specified second cells.

12. The method according to claim 11, wherein the specifying second cells step is further performed by specifying the second cells by detected side scattered light.

* * * * *